United States Patent
Du-Nour

(10) Patent No.: US 10,656,085 B2
(45) Date of Patent: May 19, 2020

(54) HIGH SENSITIVITY REAL-TIME BACTERIAL MONITOR

(71) Applicant: BACTUSENSE TECHNOLOGIES LTD., Timrat (IL)

(72) Inventor: Ofer Du-Nour, Timrat (IL)

(73) Assignee: BACTUSENSE TECHNOLOGIES LTD., Timrat (IE)

( * ) Notice: Subject to any disclaimer, the term of this patent is extended or adjusted under 35 U.S.C. 154(b) by 0 days.

(21) Appl. No.: 15/565,161

(22) PCT Filed: Apr. 8, 2016

(86) PCT No.: PCT/IL2016/050377
§ 371 (c)(1),
(2) Date: Oct. 8, 2017

(87) PCT Pub. No.: WO2016/162874
PCT Pub. Date: Oct. 13, 2016

(65) Prior Publication Data
US 2018/0100798 A1 Apr. 12, 2018

Related U.S. Application Data

(60) Provisional application No. 62/178,355, filed on Apr. 8, 2015.

(51) Int. Cl.
| | |
|---|---|
| *G01N 21/47* | (2006.01) |
| *G01N 21/45* | (2006.01) |
| *A61B 5/00* | (2006.01) |
| *G01D 5/26* | (2006.01) |
| *G02B 21/06* | (2006.01) |
| *G02B 21/36* | (2006.01) |

(52) U.S. Cl.
CPC ....... *G01N 21/4788* (2013.01); *A61B 5/7257* (2013.01); *G01D 5/266* (2013.01); *G01N 21/45* (2013.01); *G01N 21/4738* (2013.01); *G02B 21/06* (2013.01); *G02B 21/362* (2013.01); *G01N 2021/458* (2013.01); *G01N 2021/4726* (2013.01); *G01N 2021/4797* (2013.01); *G01N 2201/0446* (2013.01)

(58) Field of Classification Search
CPC .................................................. G01N 21/4788
See application file for complete search history.

(56) References Cited

U.S. PATENT DOCUMENTS

| | | | |
|---|---|---|---|
| 5,486,701 A * | 1/1996 | Norton | G01B 11/0625 250/372 |
| 5,738,825 A | 4/1998 | Rudigier et al. | |
| 6,248,539 B1 | 6/2001 | Ghadiri et al. | |
| 7,759,129 B2 | 7/2010 | Sailor et al. | |
| 8,274,643 B2 | 9/2012 | Sailor et al. | |
| 8,349,617 B2 | 1/2013 | Weiss et al. | |
| 2002/0192680 A1 | 12/2002 | Chan et al. | |
| 2003/0027328 A1 | 2/2003 | Cunningham et al. | |
| 2003/0104512 A1 | 6/2003 | Freeman et al. | |
| 2005/0019956 A1 | 1/2005 | Martin et al. | |
| 2005/0048599 A1 | 3/2005 | Goldberg et al. | |
| 2005/0213089 A1 | 9/2005 | Margalith et al. | |
| 2006/0234391 A1 | 10/2006 | Weiss et al. | |
| 2006/0255008 A1 | 11/2006 | Link et al. | |
| 2006/0276047 A1 | 12/2006 | Ouyang et al. | |
| 2007/0108465 A1 | 5/2007 | Pacholski et al. | |
| 2007/0172894 A1 | 7/2007 | Genick et al. | |
| 2008/0020480 A1* | 1/2008 | Lin | G01N 21/253 436/164 |
| 2009/0180932 A1 | 7/2009 | Angeley | |
| 2010/0246007 A1 | 9/2010 | Moon et al. | |
| 2010/0279886 A1 | 11/2010 | Fauchet et al. | |
| 2012/0214707 A1 | 8/2012 | Ymeti et al. | |
| 2012/0268823 A1 | 10/2012 | Morhard et al. | |
| 2013/0338303 A1 | 12/2013 | Quint et al. | |

(Continued)

FOREIGN PATENT DOCUMENTS

| | | |
|---|---|---|
| CN | 1140763 | 1/1997 |
| CN | 1352388 | 6/2002 |
| CN | 102519908 | 6/2012 |

(Continued)

OTHER PUBLICATIONS

Fu Nature Biotechnology, 1999, 17:1109-1111.*
Naama Massad-Ivanir et al: "Trap and track: designing self-reporting porous Si photonic crystals for rapid bacteria detection", The Analyst, vol. 139. No. 16, Jan. 1, 2014, p. 3885-3894.
Y. Mirsky et al: "Optical biosensing of bacteria and cells using porous silicon based, photonic lamellar gratings", Applied Physics Letters, vol. 103. No. 3, Jan. 1, 2013.
Holgado M. et al. 2007. Optical characterization of extremely small volumes of liquid in sub-micro-holes by simultaneous reflectivity, ellipsometry and spectrometry. Optics Express vol. 15, pp. 13318-13329.
Pacholski C et al, Biosensing using porous silicon double-layer interferometers: Reflective interferometric fourier transform spectroscopy, Journal of the American Chemical Society, Aug. 24, 2005, pp. 11636-11645, vol. 127, No. 33, American Chemical Society, US.

(Continued)

*Primary Examiner* — Bin Shen
(74) *Attorney, Agent, or Firm* — The Roy Gross Law Firm, LLC; Roy Gross

(57) ABSTRACT

Systems for the monitoring of bacterial levels in samples, using spectral analysis of the light diffracted from a substrate with an ordered array of pores having diameters enabling the targets to enter them. The trapping pore array is cyclically illuminated by light of different wavelengths, and the light diffracted from the pore array is imaged by a 2-dimensional detector array, with one pixel, or a small group of pixels receiving light from each associated pore. The temporal sequence of frames provides a series of images, each from the reflection of a different wavelength. A time sequenced readout of the signal from the pixel or pixels associated with each pore region, provides a spectral plot of the reflected light from that pore region. Spectral analysis of the light intensity from this series of different wavelength enables the effective optical thickness (EOT) of each pore to be extracted.

9 Claims, 4 Drawing Sheets

(56) References Cited

U.S. PATENT DOCUMENTS

2014/0011223 A1    1/2014  Sjong et al.

FOREIGN PATENT DOCUMENTS

| | | | |
|---|---|---|---|
| CN | 102539486 | 7/2012 | |
| CN | 102713578 | 10/2012 | |
| EP | 2327955 | 6/2011 | |
| WO | 2010099805 | 9/2010 | |
| WO | 2013165398 | 11/2013 | |
| WO | 2014155381 | 10/2014 | |
| WO | WO-2014155381 A1 * | 10/2014 | ............ G01D 5/266 |
| WO | 2016142878 | 9/2016 | |

OTHER PUBLICATIONS

X.G. Zhang, Morphology and Formation Mechanisms of Porous Silicon, Journal of the Electrochemical Society, Dec. 9, 2003, p. C69, XPO55309486, vol. 151, No. 1.

M. Holgado et al, Micro-nano photonic biosensors scalable at the wafer level, Optical Sensing II, Feb. 12, 2009, p. 72200P, XP055311429, vol. 7220, US.

Jane A et al, Porous silicon biosensors on the advance, Trends in Biotechnology, Feb. 27, 2009, pp. J30-J239, XP026029660, vol. 27, No. 4, Elsevier Publications, Cambridge, GB.

PCT International Search Report and Written Opinion for PCT/IL2014050317, Jul. 11, 2014.

Supplementary European Search Report for EP 14773472, dated Oct. 26, 2016.

* cited by examiner

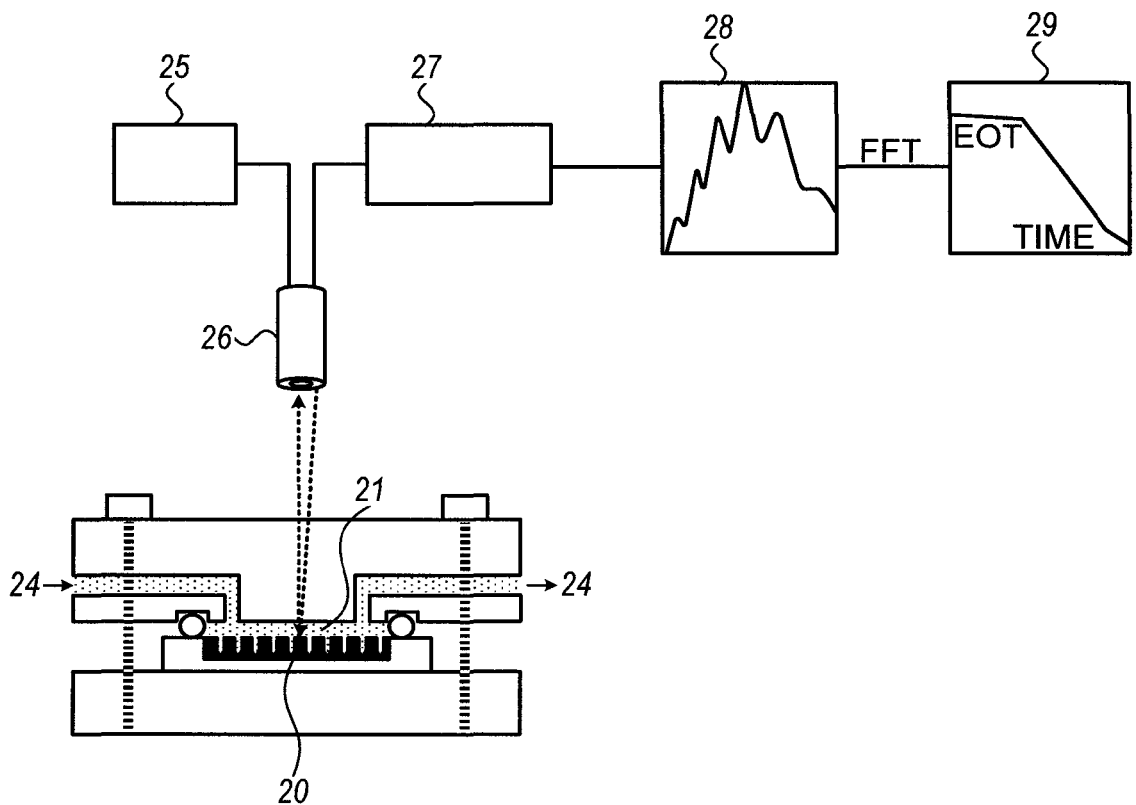
FIG. 1 (PRIOR ART)
FIG. 2
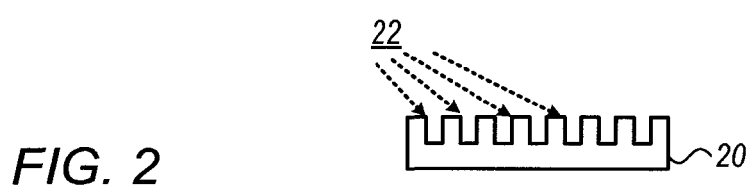
FIG. 3
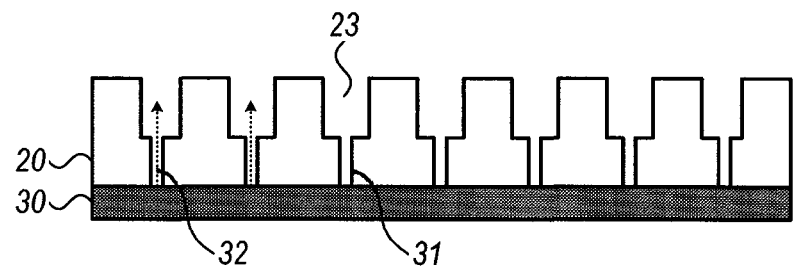

HIGH SENSITIVITY REAL-TIME BACTERIAL MONITOR

CROSS-REFERENCE TO RELATED APPLICATIONS

This application is a U.S. National Phase Application under 35 U.S.C. 371 of International Application No. PCT/IL2016/050377, which has an international filing date of Apr. 8, 2016, and which claims the priority benefit of U.S. Provisional Patent Application No. 62/178,355, filed Apr. 8, 2015, the description of which is hereby incorporated by reference.

FIELD OF THE INVENTION

The present invention relates to the field of bacterial detection in host solutions, especially for use in real time assessment of bacterial levels, such as in flow process manufacturing.

BACKGROUND OF THE INVENTION

In International Publication number WO 2014/155381 for "Method and Apparatus for Bacterial Monitoring", there is described an apparatus and method for detection of the concentration of bacteria and cells. A schematic illustration of a system using described in that publication is shown in FIG. 1. The system incorporates a substrate 20 with an ordered array of wells or pores having diameters to fit the size of the targets. The substrate may be a periodic macro-PSi array structure (MPSiAS) illuminated with a broadband, white light source 25, which generates a large illumination spot on the substrate, thereby illuminating a substantial portion of the substrate. The drawing of FIG. 1 shows a single ray from the source 25 and reflected back from a pore region of substrate to the single detector 26, which, in the example system of FIG. 1, is positioned in the same housing as the illuminating source unit. It is to be understood though that the optical illuminating and detection system covers all or a major part of the substrate. The host analyte 24 whose bacterial content is to be measured, is flown across the surface 21 of the substrate, in a direction essentially parallel to the surface of the array, and the bacteria in the host analyte enter the wells of the substrate by random motion away from the direction of flow. The reflected light diffracted from either the whole of the substrate, or a substantial part of it, is detected 26 and spectrally analyzed 27, 28 to provide the effective optical depth of the wells. Fast Fourier Transform analysis 28, 29 may be used for the optical analysis, and the amplitude of the reflected interference light at the detected effective optical depth provides a measure of the bacterial filling factor of the wells. Entry of target elements into wells is detected by the change in the effective optical depths of the wells. The detection may be performed in real time, such that production line bacterial monitoring may be achieved.

However, the apparatus described in that publication has a number of operational disadvantages, as a result of which, the lowest concentration of bacteria that can be measured within a reasonable time is limited. The apparatus has been shown to be capable of bacterial detection down to a concentration of approximately $10^6$ cells/ml of live bacteria. The requirements of both the food industry and the water industry are, however, as low as 100 cells/ml., or even lower. This may make that device commercially disadvantaged.

In WO 2014/155381, since the liquid sample flows over and essentially parallel to the surface of the Macro-Porous Silicon Array Structure (MPSiAS), the bacteria can enter the pores and collect there by actively directing themselves, using their motility, into the pores. For a flow direction parallel to the surface of the array, motion of the bacteria into the pores is, in the absence of any external; influence, such as a food concentration, only achieved by the self-motion of the bacteria. Such self-motion is known to be randomly directed with an average path of the order of 30µ before the bacteria change direction, which occurs every 1 sec. or so. This means that bacteria floating in the solution further than 30µ from the surface of the array, will have a significantly lower probability of entering the pores.

The rate of bacteria entry into the pores can be calculated by:

$$S_{in} = \int Q(I) * P(I) \tag{1}$$

where $S_{in}$ is the rate of bacteria going into the pores,
Q(I) is the concentration of bacteria at a distance I from the surface of the array, and
P(I) is the probability of the bacteria, at a distance I, to enter into a pore.
The integral is taken from I=0 at the array surface to I=∞.

For example, if the bacterium is under no external influence that would offer it a proffered direction in which to move, i.e. that its motion is completely random, the chance that it will move in a given direction is ¼π. The chances of a bacterium, located 30µ above a pore of dimension 2µ×2µ, to enter the pore, would therefore be $$P(30\mu) = (2\mu/30\mu)^2/4\pi \tag{2}$$

However, in the same way as bacteria enter the pores, they also have a chance to leave the pores, whether by randomly flowing back into the fluid flow outside of the pores or by actively moving themselves out.

The rate of bacteria exiting is given by:

$$S_{out} = \int Q'(I) * P'(I) \tag{3}$$

where $S_{out}$ is the rate of pore emptying,
Q'(m) is the concentration of bacteria in the pore at a depth m from the top of the pores and
P'(m) is the probability of the bacteria, at a depth m, to exit a pore.
The integral is taken from m=0 at the array surface, to m=D, where D is the average pore depth.

The filling rate of the bacteria is:

$$S = S_{in} - S_{out} \tag{4}$$

The optical signal, as described in the WO 2014/155381 reference, is the interference pattern generated between the collective reflection of broadband light from the bottom surfaces of all the pores, included within the light beam, and the surfaces of the substrate between the pores. When pores start filling with bacteria, the collective reflection pattern changes from a pattern of EOT(n) pores filled just with the sample solution (where n is the number of pores included in the light beam) to:

$$EOT = EOT'(m) + EOT(n-m) \tag{5}$$

where EOT'(m) is the reflection coming from m pores filled with bacteria. The greater the number of pores occupied with bacteria, the more the EOT changes, until almost all the pores are filled, and no further change of EOT is expected. The rate of change is proportional to the occupancy rate S and obviously decreases as the concentration Q decreases. For lower concentrations, using the apparatus of the WO 2014/155381 reference, it transpires that the EOT change rate is so low that it is not easily detected within a practical time frame. Using the WO 2014/155381 prior art system, because of the integrating nature of the detection process, it may be necessary to reach a bacterial filling factor of several percent before the change in bacterial concentration is quantitatively detected in the spectral analysis of the integrated light reflected from the whole illuminated region of the substrate. Since on-line monitoring of processes, such as on a food production line, require the detection of bacterial concentrations at levels lower than $10^2$ cells/ml which is four orders of magnitude or more below the level of detection achieved by the WO 2014/155381 system, and in a time frame short enough not to result in undue wastage should a contamination be detected, the level of sensitivity provided by the prior art system may be insufficient for such use.

There therefore exists a need for a method and apparatus to increase detection sensitivity of the bacteria, and thus to overcome at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems for the detection and monitoring of bacterial levels in samples, using spectral analysis of the light diffracted from a substrate with an ordered array of wells or pores having diameters selected such that the targets can enter them. The disclosure firstly presents methods and apparatus, for increasing the rate of capture of the bacteria for a given concentration of bacteria in the sample, over that obtained with the apparatus shown in the prior art, such as in the WO 2014/155381 system. This is achieved by four methods described in this disclosure—
(i) Aiming of the flow direction of the host analyte such that it impacts the trapping array pores at an angle of incidence other than parallel to the array surface.
(ii) Adding a layer of nutrient to the bottom of the pores so that the bacteria, having the ability to move, under their own propulsion, in the direction of food source, will actively move into the pores, instead of entering randomly.
(iii) Increasing the concentration of the bacteria flowing towards the pores, over that in the host solution, by using a selective membrane filter to direct the host analyte in a direction away from the pore entrances, but stopping the bacteria from proceeding in that direction, such that the bacteria impact the pore entrances at a higher concentration in the remaining analyte.
(iv) Applying an electric field perpendicular to the plane of the substrate and across the width of the flow path of the bacteria-laden analyte, such that the field acting on the natural self charge on the bacteria, causes the bacteria to preferentially move in the direction of the substrate, thereby increasing the chance of their entering a pore.

However, the most effective increase in the system sensitivity is generated in the present described systems by the use of a novel optical detection configuration in which the trapping pore array is sequentially and cyclically illuminated by light of different wavelengths, and the light received after reflection from the pore array is directed onto a 2-dimensional detector array, which images the light with one pixel, or a small group of pixels receiving light from each associated pore. The temporal sequence of frames then provides a series of images each from the reflection of a different wavelength. Thus, the time sequenced output of the light reflected from each pore region of the substrate represents a spectral plot of the reflection from that region spread out along the time axis, such that a time sequenced readout of the signal from the pixel or pixels associated with each pore region, provides a spectral plot of the reflected light from that pore region. Collection and spectral analysis of the light intensity from this series of different wavelength frames for each of the pixels or groups of pixels, such as by use of the fast Fourier transform, enables the effective optical thickness (EOT) of each pore to be extracted. The number of sequential frames selected to perform the spectral analysis for each pixel or group of pixels, is synchronized with the number of separate wavelengths used sequentially to illuminate the substrate, and hence with the cycle time of the wavelength sequence, such that each spectral analysis takes place over the same sequence of changing wavelengths for each pixel or group of pixels, and for each wavelength change cycle. From the change in each one of the EOT's, the percentage of bacterial presence in each one of the pores can be obtained. By detecting the EOT of essentially each pore independently on a different pixel or group of pixels of the detector array, it becomes possible to detect any rise in the bacterial concentration based on change in the EOT of individual pores, substantially sooner than using the prior art system shown in the WO 2014/155381 reference, which must await an integrated change in intensity over the entire illuminated surface of the substrate before any change is noted in the reflection spectrum that would enable the change in the average EOT to be determined. The novel optical configuration of the system of the present disclosure thus differs significantly from the prior art optical detection methods, where a wide beam of white light is used to illuminate the entire pore array, or a substantial portion thereof, and the resulting interference spectrum from the whole illuminated area is collected in a single detector, and the spectrum is Fourier transformed to generate a plot of the integrated effective optical thicknesses of the pores array with time, and hence the concentration of bacteria trapped.

In the system described above, the spectrally resolved light reflection spectrum has been obtained by illuminating the substrate with a sequential series of different wavelengths, and detecting these wavelengths with a 2-dimensional imaging array, which can be a black and white array. However, a time-sequenced spectral plot can equally well be obtained by illuminating the substrate with white light and performing the time sequenced wavelength detection scheme on the reflected light before detection on the 2-dimensional imaging array. In such a scheme, the wavelength filter selecting the sequentially detected wavelengths is disposed in the reflected light optical path, most conveniently in front of the imaging array. The position of the wavelength selecting component can be determined by the most convenient structural arrangement of the system. The wavelength selector can be a rotating filter wheel, or a liquid crystal tunable filter, or any other suitable tunable wavelength filter component.

There is therefore provided in accordance with a with an exemplary implementation of the devices described in this disclosure, a method for detecting target elements in a host analyte, the method comprising:
(i) providing a substrate containing an ordered array of pores formed in its surface, at least some of the pores having lateral dimensions enabling the target elements to fit therein,
(ii) directing the host analyte over the surface of the substrate, such that at least one of the target elements can enter at least one of the pores,
(iii) Illuminated the pore array by light containing different wavelengths, (iv) imaging light diffracted from the pore array by a two dimensional detector array, with a pixel or a group of pixels receiving light from an associated pore,
(v) generating a temporal sequence of frames, each from the diffraction of a different wavelength,
(vi) generating a time sequenced readout of the signal from the pixel or group of pixels associated with the pore region, and
(vii) spectrally analyzing the time sequenced readout to enable the effective optical thickness of the associated pore to be determined.

In such a method, the temporal sequence of frames, each from the diffraction of a different wavelength, may be generated either by filtering the illuminating light to generate a sequence of illuminating wavelengths, or by filtering the light diffracted from the pore array to generate a sequence of detected wavelengths. In either of these cases, the filtering may be performed either by a filter wheel or a tunable liquid crystal filter.

In other implementations of the above described methods, the effective optical thickness of the associated pore may be determined by performing a Fourier transform on the time sequenced readout of the signal from the pixel or group of pixels associated with the pore.

Furthermore, in any of these methods, the host analyte including the target elements may be directed, prior to being directed over the surface of the substrate, in a stream in contact with a filter membrane which enables the host analyte to pass therethrough but not the target elements, such that the concentration of the target elements in the stream increases with passage of the stream towards the surface of the substrate. Additionally, the host analyte including the target elements may be directed towards the surface of the substrate in a direction such that it impinges the surface at an angle substantially different from a grazing angle.

Additional implementations may involve any of the above methods, in which the pores are provided with a material which preferentially attracts the target elements, the material being disposed in the pores remotely from the surface of the substrate.

Any of the methods may further comprise the application of an electric field generally perpendicular to the plane of the substrate, such that any target elements carrying a charge are preferentially attracted to enter the pores. Finally, in any of the above described methods, the target elements may be bacteria.

Further example implementations may involve a system for detecting target elements in a host analyte, the system comprising:
(i) a substrate containing an ordered array of pores formed in its surface, at least some of the pores having lateral dimensions enabling the target elements to fit therein,
(ii) a flow system for directing the host analyte over the surface of the substrate,
(iii) an Illuminating source generating light containing different wavelengths, the source being disposed such that the substrate is located in the light path of the illumination,
(iv) a two dimensional pixelated array imaging light diffracted from the substrate, a pixel or a group of pixels receiving light from an associated pore,
(v) a tunable filter disposed in the light path between the illuminating source and the detector array, the filter generating a temporal sequence of wavelengths from the illumination,
(vi) a frame recording system, configured to generate a temporal sequence of image frames of the pixelated array, each frame being recorded at a different wavelength,
(vii) a spectral analyzer configured to extract from the temporal sequence of image frames, a spectral signal sequence from the pixel or group of pixels receiving light from the associated pore, and
(viii) a processor adapted to determine from the spectral signal sequence, a measure of the effective optical thickness of that pore associated with the pixel or group of pixels.

In such a system, the tunable filter generating a temporal sequence of wavelengths from the illumination, may be disposed either in the path of light incident on the substrate, or in the path of light diffracted from the substrate. In either case, the filter may be either a filter wheel or a tunable liquid crystal filter.

In other implementations of the above described systems, the effective optical thickness of the associated pore may be determined by performing a Fourier transform on the spectral signal sequence of the signal from the pixel or group of pixels associated with the pore.

Furthermore, in any of these systems the host analyte including the target elements may be directed, prior to being directed over the surface of the substrate, in a stream in contact with a filter membrane which enables the host analyte to pass therethrough but not the target elements, such that the concentration of the target elements in the stream increases with passage of the stream towards the surface of the substrate. Additionally, the host analyte including the target elements may be directed towards the surface of the substrate in a direction such that it impinges the surface at an angle substantially different from a grazing angle.

Additional implementations may involve any of the above systems, in which the pores may comprise a material which preferentially attracts the target elements, the material being disposed in the pores remotely from the surface of the substrate.

Any of the above described systems may further comprise electrodes for the application of an electric field generally perpendicular to the plane of the substrate, such that any target elements carrying a charge are preferentially attracted to enter the pores. Finally, in any of the above described systems, the target elements may be bacteria.

Another method described in the present disclosure may be for the purpose of detecting target elements in a host analyte, the method comprising:
(i) providing a substrate containing an ordered array of pores formed in its surface, at least some of the pores having lateral dimensions enabling the target elements to fit therein,
(ii) directing the host analyte including the target elements over the surface of the substrate, such that at least one of the target elements can enter at least one of the pores,
(iii) illuminating at least part of the substrate with light,
(iv) detecting illumination diffracted from the substrate with a two dimensional pixelled array, to provide a temporally sequenced, spectrally coded series of frames, each frame showing the illumination diffracted from the substrate at sequential time intervals,
(v) generating from the temporally sequenced series of frames, a reflected spectrum signal sequence for separate pixels or predetermined groups of pixels of the array, and
(vi) determining from the reflected spectrum signal sequences, a measure of the effective optical depth of those pores associated with the separate pixels or predetermined groups of pixels,
wherein the spectral coding is generated either by filtering the light to generate a sequence of illuminating wavelengths, or by filtering the detected illumination to generate a sequence of detected wavelengths.

Additionally, alternative implementations of any of the systems of the present disclosure may be a system for detecting target elements in a host analyte, the system comprising:
(i) a substrate containing an ordered array of pores formed in its surface, at least some of the pores having lateral dimensions enabling the target elements to fit therein,
(ii) a flow system for directing the host analyte including the target elements over the surface of the substrate,
(iii) an illuminating source, disposed such that the substrate is located within the path of light emitted by the source,
(iv) a two dimensional pixelated array detecting illumination diffracted from the substrate,
(v) a tunable filter disposed in the light path between the illuminating source and the detector array, the filter generating a temporal sequence of wavelengths to the detected illumination,
(vi) a frame recording system, configured to generate a temporal sequence of image frames of the pixelated array, each frame being recorded at a different wavelength of a the temporal sequence, such that the frames show the illumination diffracted from the substrate at a different wavelength of the temporal sequence of wavelengths,
(vii) a spectral analyzer configured to extract from the temporal sequence of image frames, a reflected spectrum signal sequence for separate pixels or predetermined groups of pixels of the array, and
(vii) a processor adapted to determine from the reflected spectrum signal sequences, a measure of the effective optical depth of those pores associated with the separate pixels or predetermined groups of pixels.

BRIEF DESCRIPTION OF THE DRAWINGS

The presently claimed invention will be understood and appreciated more fully from the following detailed description, taken in conjunction with the drawings in which:

FIG. 1 shows a schematic illustration of a prior art system as shown in International Publication number WO 2014/155381;

FIG. 2 illustrates how the probability of impact of the bacterial content on the pore array is increased by aligning the flow direction to impinge at an angle on the surface of the pore array;

FIG. 3 illustrates a further implementation for creating motion of the bacteria in the preferred direction toward the pores by use of a nutrient layer at the bottom of the pores;

DETAILED DESCRIPTION

Figure 4:
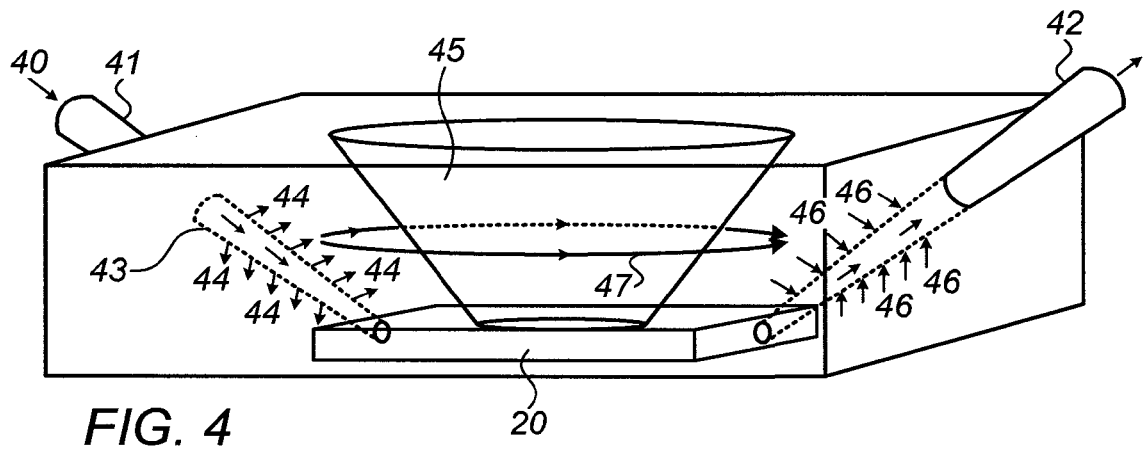
FIG. 4 illustrates schematically a device using a filter membrane to increase the probability of trapping bacteria in the pores, by increasing the effective concentration of bacteria in the analyte fluid flowing across the entrance of the pores.

Reference is now made to FIG. 1, which illustrates schematically a prior art system such as that described in International Publication number WO 2014/155381. Details of the structure of the system have been given in the Background Section of this disclosure. Optically, a broadband white light source illuminates the array, and the zero order reflected light is collected from a wide area of the array, and directed from the detector element 26 to a spectrometer. The spectrometer converts the light to a set of electrical signals proportional to the intensity of each wavelength included in the incoming light. The detected light is a combination of the reflected light from all the pores under the beam. The percentage of pores occupied by bacteria changes the intensity of the EOT signal proportionally to the total number of pores under the beam. It is necessary to wait until at least a few percent of the pores change their reflection pattern due to bacteria population, before a distinctive change in the EOT is noticed.

Reference is now made to FIG. 2, which illustrates how, according to a first exemplary arrangement, the probability of impact of the bacterial content on the pore array is increased by aligning the flow direction 22 to impinge on the surface of the pore array at an angle far from the glancing angle used in the prior art implementation of FIG. 1, such that the probability of bacterial entry into the pores is increased. In the implementation of FIG. 2, the entry of a bacterium into a pore may be achieved not only by means of its own motility, but also by the flow direction 22 of the analyte forcing it to impinge on and enter into a pore. The flow should be slow enough that the solution current within the pores will remain moderate to allow the bacteria to attach to the walls of the pores before they could be swept out of the pores again by the force of the flow. The velocity inside the pore should be less than 30 µ/sec, which is the order of the bacteria self-motion velocity.

Reference is now made to FIG. 3, which illustrates a further implementation for creating motion of the bacteria in the preferred direction toward the pores. It is known that the motility of bacteria in non-neutral solutions can be used to encourage movement of the bacteria towards or away from parts of the solution with higher concentrations of certain chemicals. This motion is known as Chemotaxing. For example, in the case of a gradient of concentration of bacterial nutrient, which is the material which the bacteria use as food, the bacteria motion will not be completely random in all direction, but the bacteria will prefer to move toward the higher concentration of nutrients. In the case of material with poisoning effects on the bacteria, a motion with preferred direction away from the high concentration is observed.

FIG. 3 illustrates a method by which this effect can be used to create preferred motion of the bacteria toward the array, by creating a high concentration of nutrients in the pores 23. At the bottom of the pores a layer of nutrient material is provided such as by making the pores extend through their bottom end, and positioning a layer of nutrient 30 beneath the substrate 20, as shown in FIG. 3. The nutrient layer 30 may either be positioned at the bottom of simple single diameter pores, or a stepped pore structure may be used, with micro-channels 31 from the bottom of the pores 23 to the bottom of the array substrate 20. This can be readily achieved by means of an additional etching step to the pore etching process. Positioning the pore array substrate 20 on top of an additional substrate composed of nutrient material 30, will cause the nutrients to diffuse 32 from the nutrient substrate into the pores, making the pores nutrient rich. The bacteria in the solution above the array will have now the motivation to move toward the array and into the pores. The probability P(I) for bacteria to move towards the array is now higher than the probability that they move away from the array, and in addition, the length of the leg of linear motion before a bacterium changes direction is also substantially longer.

Reference is now made to FIG. 4, which illustrates schematically a further implementation for increasing the probability of trapping bacteria in the pores, by increasing the effective concentration of bacteria in the analyte fluid flowing across the entrance of the pores. In the analysis cell of FIG. 4, a special filtration system is used in order to direct the host analyte with an increased concentration of the bacteria in the direction where it will impinge on the top of the pore array, while allowing the host solution itself (referred to as the permeate) to preferentially move in another direction, avoiding passage over the substrate, such that the bacteria content of the analyte moving towards the substrate (referred to as the Retentate) increases as the analyte itself is filtered out of the flow towards the substrate.

Referring to FIG. 4, the solution 40 enters through an inlet port 41 on the left-hand side of the drawing of the device, passes across the surface of the MPSiAS pored substrate 20, and exits the device through and outlet port 42 on the right-hand side of the drawing of the device. The inlet flow is directed down a passage 43 towards the pored substrate. The passage 43 may be tapered such that the narrowing of the passage causes an increased pressure of the solution. The envelope of the passage 43, through which the solution is passing, comprises a filter membrane which allows molecules of the solution to pass through 44, but blocks the passage of bacteria, which continue downwards towards the MPSiAS 20. As a result, the Primate solution tends to short-circuit 47 the path through the device from input to output port, flowing around the central opening 45 through which the optical illumination and detection is performed, and in so doing, increases the bacterial concentration of the Retentate solution which continues to flow down the input passage 43 and across the surface of the pored substrate 20. When finally arriving at the pored array 20, the bacteria concentration in the solution may be orders of magnitude higher than that of the solution 40 entering the device, thereby increasing the probability of bacteria entering the pores by the same concentration ratio increase.

A numerical example shows this effect quantitatively. Assuming that the height of the cell above the array is 0.1 mm, and the array width is 10 mm, the cross section of flow above the array is 1 mm$^2$. If the entrance is designed such that the cross section of the solution flowing through the input port is 100 mm$^2$, then using the proper membrane design (pore size and surface area), the bacterial concentration can increase by two orders of magnitudes before reaching the array, thereby increasing the detection sensitivity of the device by the same two orders of magnitude.

Figure 5:
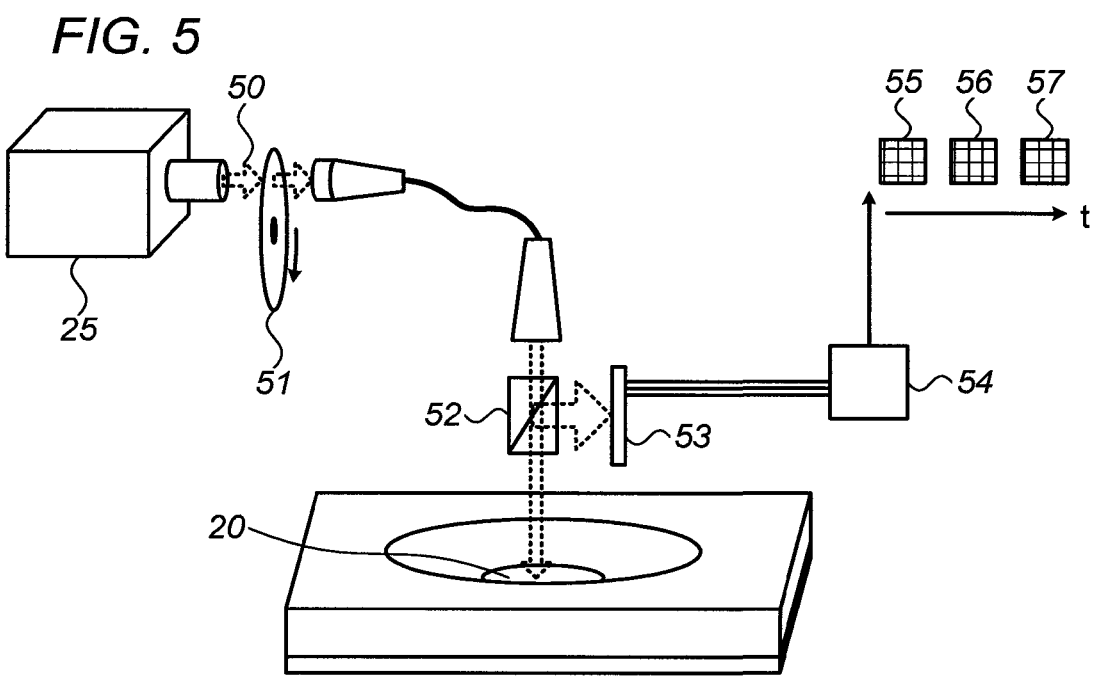
FIG. 5 is a schematic illustration of a complete optical detection system for bacterial monitoring using a sequentially scanned wavelength source for illuminating the sample.

Reference is now made to FIG. 5, which is a schematic illustration of the complete optical detection system for bacterial monitoring of a host solution. The system differs from that shown in the WO 2014/155381 prior art, primarily in that the white light, broadband illumination source beam 50 generated in the illumination source 25 is passed through a rotating filter wheel 51, or any other tunable filter device for generating a sequentially changing wavelength beam. The sequentially variable wavelength beam may be directed towards the array 20 through a beam splitter 52. The zero order reflected light, from all the pores, is directed back through the beam splitter and imaged on a CCD array 53, which can be a 'black-and-white' detector array. The frame received on the CCD is now a 2D map of the interference reflection of each point on the array, at the selected wavelength. The CCD used may conveniently be a widely available conventional array, having 1 or more Megapixels, and having a refresh rate of a low few tens of Hz, though it is to be understood that these values are not meant to limit the scope of the invention, but merely represent currently readily available, low-cost technology. Storing the frame in a frame stacker 54 and repeating the operation with each new wavelength, generates a temporal set of frames of 2D images of the reflection from the array, each one at a different wavelength, as indicted by the sample frame images 55, 56, 57, each representing the 2-D array image at successive time intervals, a different illuminating wavelength being present at each successive time interval. Processing the images and collecting the reflection of each pixel at a different wavelength, generates a 3D array of spectra of all the pixels, two dimensions being of the 2-D array of pixels in each frame, and the third dimension being the time scale over which the sequence of frames are stored in the frame stacker 54.

Since each pixel has collected the spectrum from a single point of the array, the change of the EOT generated from that specific pixel represent changes at the respective pore region of the array. It is possible to design the optics such that it will represent a small group of pores, down to one pore per pixel. Capturing of one bacterium in one pore now generates a large change in the collective reflectance from a region of just a few pixels and even 100% in the case of one pore per pixel. It should be noted that the pore size for commonly monitored bacteria are of the same order of magnitude as the pixel spacing of commonly available CCD or CMOS imaging arrays, a standard pixel being about 7µ×7µ, while a suitable pore size for such bacteria is about 2µ–4µ, and the space between the pores is also 3µ–5µ. Consequently, it is possible to insert magnifying optics in the imaging path, and to either image one pore on one or several pixels or to have one pixel imaging several pores.

In an embodiment where the illuminating beam incident on the substrate is white light, and the spectral decoding is performed by means of a filter positioned in the reflected path of the illumination light, the filter wheel 51, or an alternative tunable filter device, could be positioned in front of the CCD detector array 53, instead of at the output of the illumination source 25, as shown in the implementation of FIG. 5.

Figure 6:
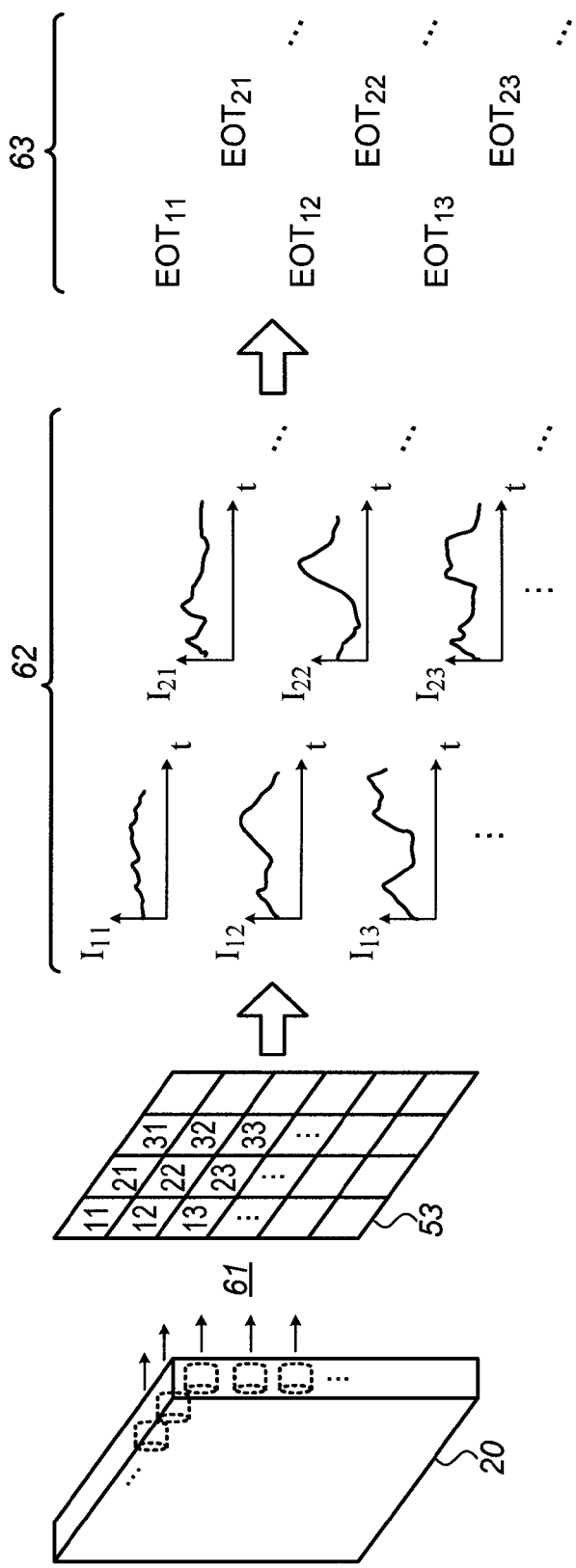
FIG. 6 is a schematic drawing showing how the analysis of the temporally changing reflected interference light from the pixels of the array can be used in order to determine the EOT of individual pores, and hence the bacterial concentration of the solution being monitored.

Reference is now made to FIG. 6, which is a schematic drawing showing how the analysis of the temporally changing reflected interference light from the pixels of the 2D imaging array can be used in order to determine the EOT of individual pores, and hence the bacterial concentration of the solution being monitored. The light 61 reflected from a pored substrate 20 impinges on the pixels of a 2-D imaging array such as a CCD. In order to explain the information extraction procedure, the pixels are marked with indices according to their column and row, as follows: 11, 12, 13, . . . ; 21, 22, 23, . . . ; 31, 32, 33, . . . ; etc. The time sequenced output of each pixel is represented by an array of light intensity measured by that pixel as a function of time, as shown by the assembly 62 of intensity/time graphs, each graph representing the time dependent output of a single pixel of the array, as follows: I11, I12, I13, . . . ; I21, I22, I23, . . . ; and so on for the whole array. Each of those time dependent plots thus represents the spectral output of each pixel, since the wavelength detected is a direct function of the time elapsed in each wavelength scan cycle. Therefore, if each time sequenced output frame is collected in a frame stacker, the individual pixel intensity/time profiles, which represent the spectral intensity output from each pore region, can be analyzed, to provide the EOT of the pore region imaged by each pixel, as shown by the assembly 63 of EOTs, as follows: EOT11, EOT12, EOT13, EOT21, EOT22, EOT23, and so on.

The result of the cyclically sequentially changing wavelength illumination beam thus results in a series of reflected zero order interference signals, one from each pixel, each having the same temporally changing wavelength sequence as the input illumination. The interference spectrum is now given for each pixel, in the form of a time varying spectral trace, and by storing the signal outputs from each separate pixel sequentially, a spectral trace is obtained for each pixel of the interference pattern from the incident illumination. The number of sequential frames stored to generate a single spectral trace is synchronized with the rotation of the filter wheel, or with the wavelength cycle used if another type of time-varying filter is used. Spectral analysis of the temporal traces from each pixel, such as by Fourier transformation, enables the values of the EOT for each pixel to be obtained separately.

The difference between this method and that of the WO 2014/155381 prior art is that whereas in the prior art, the spectral analysis is performed repeatedly at a single instance of time for light collected from the entire pore array, and from the entire light source spectrum, in the present apparatus, the spectral analysis is performed on a spectrum accumulated from a temporally selected sequence of frames over the cycle of time of the varying input illumination wavelength. The resulting output representing the changes of the EOT's of each of the pixels of the 2D image, is now an indication of the changes of the occupancy of the pore or group of pores imaged on that specific pixel. A single event of a bacterium captured in one of the pores will be clearly delineated due to its impact on the reflection of that specific pore. One measurement of the combined EOT change of large number of pores is now replaced with large number of measurements of EOT's changes of single pores. As a result, it now becomes possible to detect bacterial concentrations less than 100 cells/ml, as opposed to the $10^6$ cells\ml of the prior art system.

Since the frame rate of currently used common CCD arrays is of the order of 30 Hz, and the processing of each pixel can thus be completed in several msec., a complete wavelength plot with typically 30 different measurement wavelengths can be completed within 1 sec. In practice, signal to noise limitations do not enable a useful signal analysis to be performed on a single wavelength cycle of typically one second, and accumulation times of one minute or so are required to obtain signal levels sufficiently good to make reliable bacterial concentration measurements down to 100 cells/ml.

Figure 7:
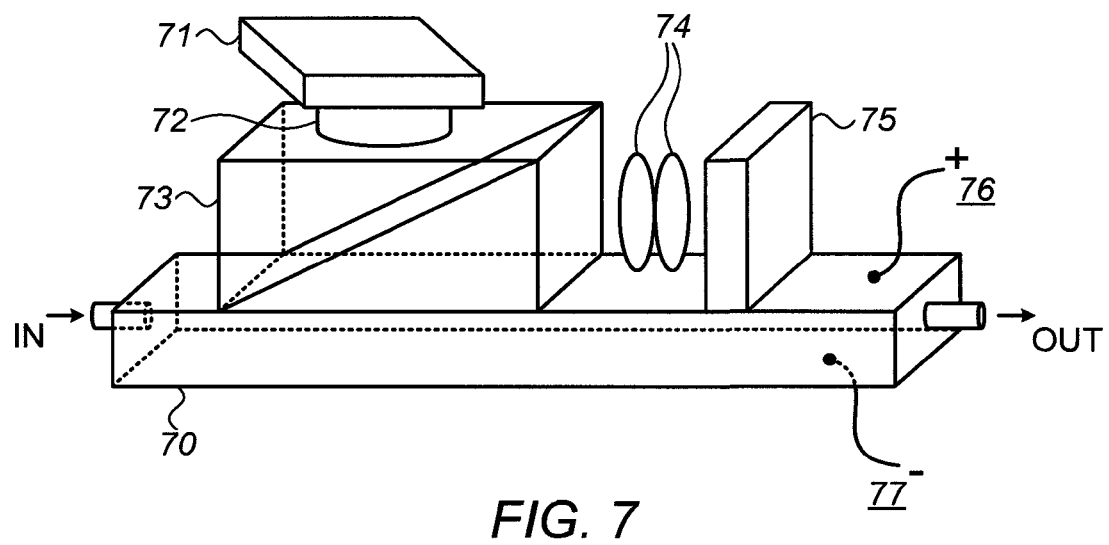
FIG. 7 illustrates a compact implementation of the bacterial monitoring system shown in FIG. 5.

Finally, reference is now made to FIG. 7, which illustrates a particularly compact implementation of the bacterial monitoring system shown in FIG. 5. In this system, the optical components are assembled on top of the flow cell 70, such that the dimensions of the monitoring system are minimized. The light source 71 projects its beam through a liquid crystal tunable filter 72, this being a very compact tunable filter having no moving parts, and from there through a beam splitter 73 onto the flow cell 70. The spectrally coded light reflected from the pores within the flow cell 70 are directed by the beam splitter 73 through an imaging lens arrangement 74 onto the CCD detector array 75. All of these optical components can be conveniently mounted in a small volume on top of the flow cell itself. Finally an electric field can be applied across the flow cell, such as by installing electrodes on the top and bottom surfaces 76, 77, of the flow cell, in order to enhance the probability of the charged bacteria from entering the pores of the substrate.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

The invention claimed is:

1. A method for detecting target elements in a host analyte, said method comprising:
providing a substrate containing an ordered array of pores formed in its surface, at least some of said pores having lateral dimensions enabling said target elements to fit therein;
directing said host analyte over the surface of said substrate, such that at least one of said target elements can enter at least one of said pores;
sequentially illuminating said array by a series of lights having different wavelengths;
capturing a sequence of images during said illuminating;
measuring time-dependent spectral reflectance intensity in a corresponding pixel in each of said sequence of images, wherein said pixel is associated with said at least one pore in said array; and
determining based, at least in part, on said measuring, an effective optical thickness of said at least one.

2. The method of claim 1 wherein said different wavelengths are generated either by (i) filtering a light source illuminating said array, or (ii) filtering light diffracted from said array.

3. The method of claim 2 wherein said filtering is performed either by a filter wheel or a tunable liquid crystal filter.

4. The method of claim 1, wherein said effective optical thickness of said at least one pore is determined by performing a Fourier transform on said time-dependent spectral reflectance intensity of said corresponding pixel in said sequence of images, wherein said pixel is associated with said at least one pore.

5. The method of claim 1, wherein said host analyte including said target elements is directed, prior to being directed over said surface of said substrate, in a stream in contact with a filter membrane which enables said host analyte to pass therethrough but not said target elements, such that the concentration of said target elements in said stream increases with passage of said stream towards the surface of said substrate.

6. The method of claim 1, further comprising directing said host analyte including said target elements towards said surface of said substrate in a direction such that it impinges said surface at an angle substantially different from a grazing angle.

7. The method of claim 1, wherein said pores are provided with a material which preferentially attracts said target elements, said material being disposed in said pores remotely from the surface of said substrate.

8. The method of claim 1, further comprising applying an electric field generally perpendicular to the plane of said substrate, such that any target elements carrying a charge are preferentially attracted to enter said pores.

9. The method of claim 1, wherein said target elements are bacteria.

* * * * *

UNITED STATES PATENT AND TRADEMARK OFFICE
CERTIFICATE OF CORRECTION

Page 1 of 1

PATENT NO. : 10,656,085 B2
APPLICATION NO. : 15/565161
DATED : May 19, 2020
INVENTOR(S) : Ofer Du-Nour It is certified that error appears in the above-identified patent and that said Letters Patent is hereby corrected as shown below:

On the Title Page

Item (73), Line 2, Assignee BACTUSENSE TECHNOLOGIES LTD. the country code should read (IL).

Signed and Sealed this
Thirtieth Day of June, 2020

Andrei Iancu
*Director of the United States Patent and Trademark Office*